United States Patent [19]

Coombs

[11] Patent Number: 5,645,715
[45] Date of Patent: Jul. 8, 1997

[54] COLLECTION TIP FOR FRACTIONATING SOLUTION GRADIENTS

[75] Inventor: David H. Coombs, Fredericton, Canada

[73] Assignee: Biocomp Instruments Inc., Fredericton, Canada

[21] Appl. No.: 433,849

[22] Filed: May 2, 1995

[51] Int. Cl.$^6$ .................................................. B01D 17/12
[52] U.S. Cl. ........................ 210/94; 210/136; 210/789; 356/246; 422/72; 422/100; 422/101; 422/103
[58] Field of Search .................. 210/94, 511, 515, 210/516, 518, 787, 789, 136; 422/72, 82.05, 100, 101, 103, 102; 436/45, 183; 356/246; 73/863.23, 864.34, 864.35

[56] References Cited

U.S. PATENT DOCUMENTS

| | | | |
|---|---|---|---|
| 3,814,248 | 6/1974 | Lawhead | 210/789 |
| 3,862,029 | 1/1975 | Joyce . | |
| 4,003,834 | 1/1977 | Coombs . | |
| 4,346,608 | 8/1982 | Olenick et al. . | |
| 4,464,254 | 8/1984 | Dojki et al. | 210/136 |
| 4,753,892 | 6/1988 | Coombs | 436/183 |
| 5,171,539 | 12/1992 | Coombs | 210/787 |
| 5,266,273 | 11/1993 | Coombs | 210/789 |

OTHER PUBLICATIONS

Albright, J.F., Anderson, N.G.: "A Method of Rapid Fractionation of Particulate Systems By Gradient Differential Centrifugation", Experimental Cell Research 15, pp. 271–281 (1958).

Anderson, N.G., Bond, H.E., Canning, R.E.: "Analytical Techniques for Cell Fractions: I. Simplified Gradient Elution Programming", Analytical Biochemistry 3, pp. 472–478 (1962).

Candler, E.L., Nunley, C.E., Anderson, N.G.: "Analytical Techniques for Cell Fractions VI. Multiple Gradient–Distributing Rotor (B–XXI)", Analytical Biochemistry 21, pp. 253–258 (1967).

Anderson, N.G., Rutenberg, E.: "Analytical Techniques for Cell Fractions: VII. A Simple Gradient–Forming Apparatus", Analytical Biochemistry 21, pp. 259–265 (1967).

Coombs, D.: "Density Gradient Fractionation by Piston Displacement", Analytical Biochemistry 68, pp. 95–101 (1975).

"Model 139 Gradient Fractionator and Model 150 Motor Controller, Owner's Manual", Biocomp Instruments, Inc., Fredericton, Canada (1995).

Primary Examiner—Joseph W. Drodge
Attorney, Agent, or Firm—Jeffrey T. Imai; Arne I. Fors; D. Doak Horne

[57] ABSTRACT

A fractionation apparatus has a displaceable piston operably mounted for displacing liquids from a centrifuge tube as the piston is inserted therein. The fractionation apparatus has a collection tip which has a seal for sealingly engaging an inner wall of the tube and has an axially extending passageway for passing liquids from within the tube to a collector as the piston is inserted into the tube. The passageway is generally a trumpet shape having a wide end and a narrow end. The wide end is presented to the liquids and the narrow end connects to the collector. The trumpet shape enhances laminar flow through the collection tip and reduced unwanted mixing between layers during fractionation.

7 Claims, 6 Drawing Sheets

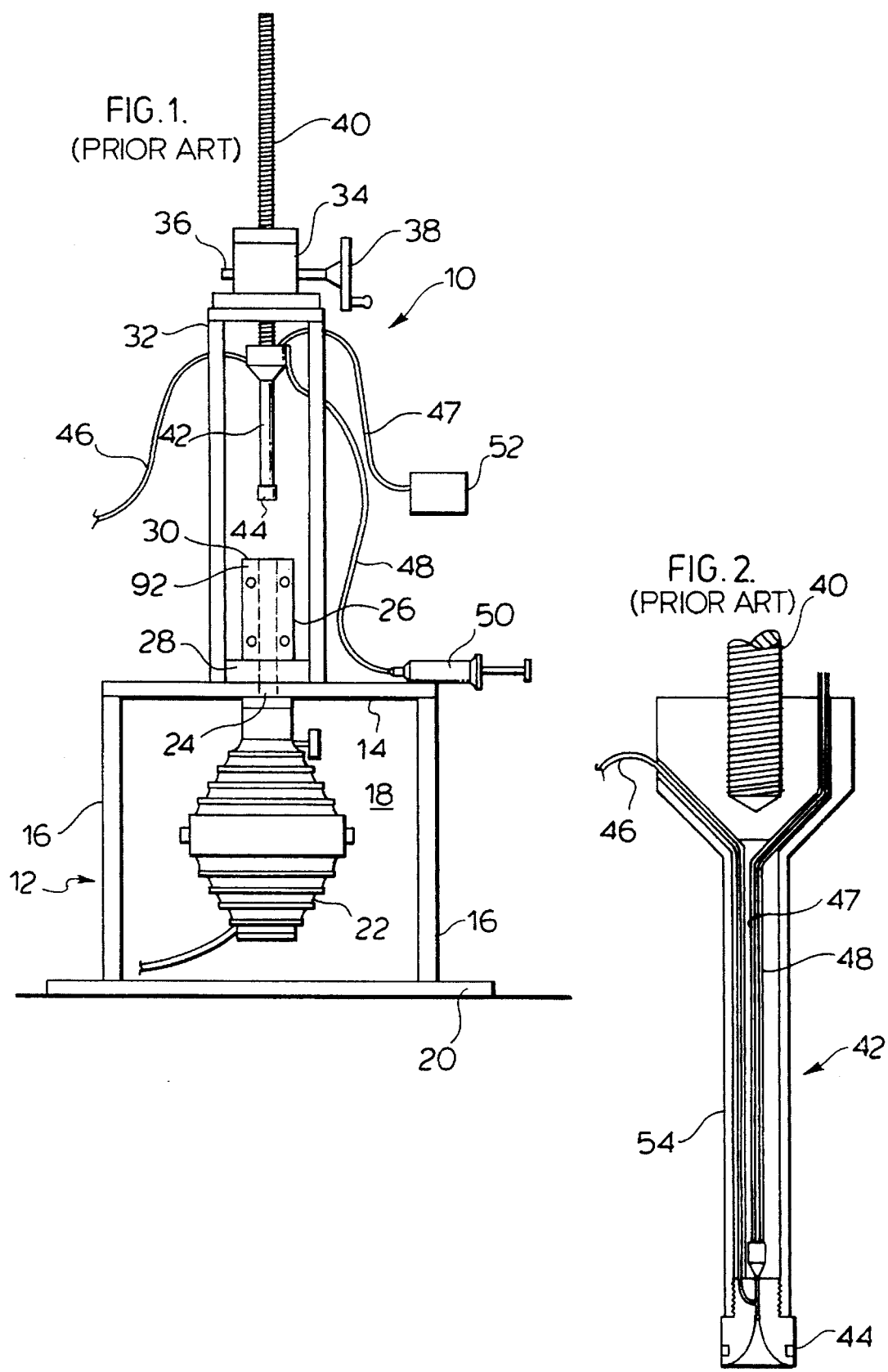

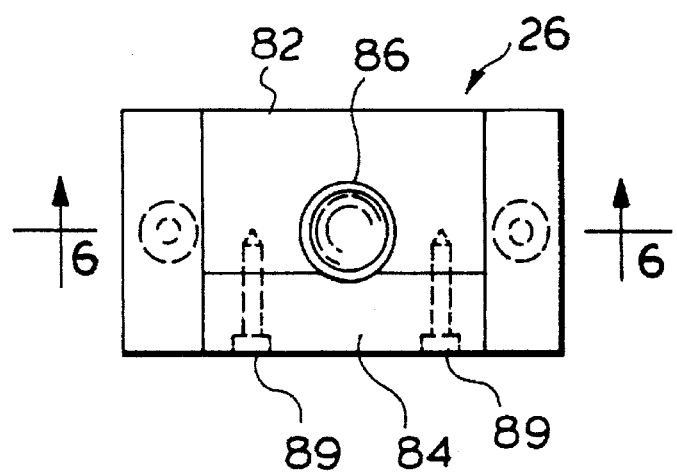
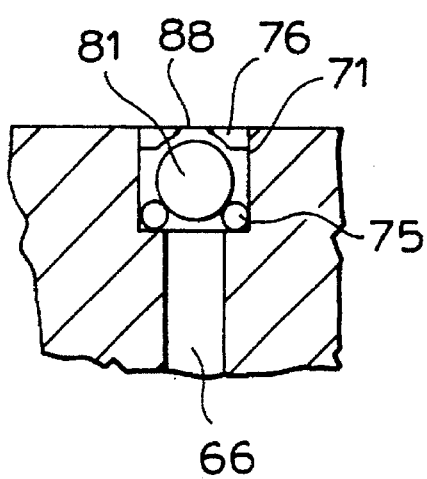
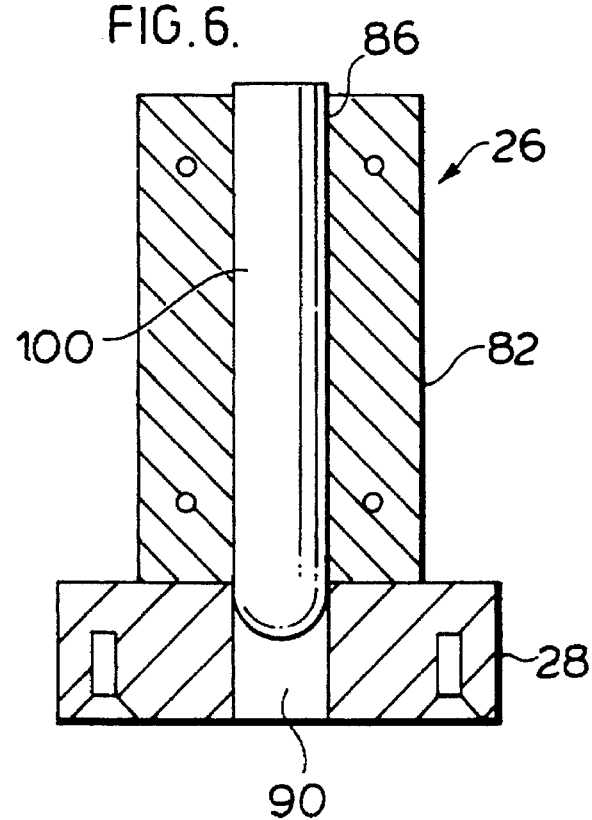

FIG. 8.
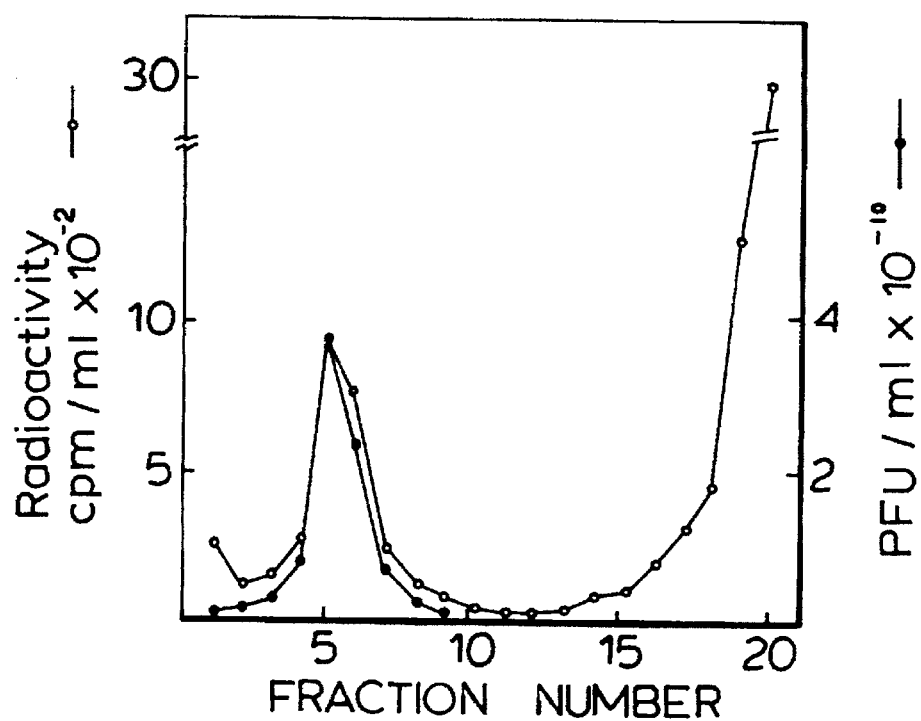
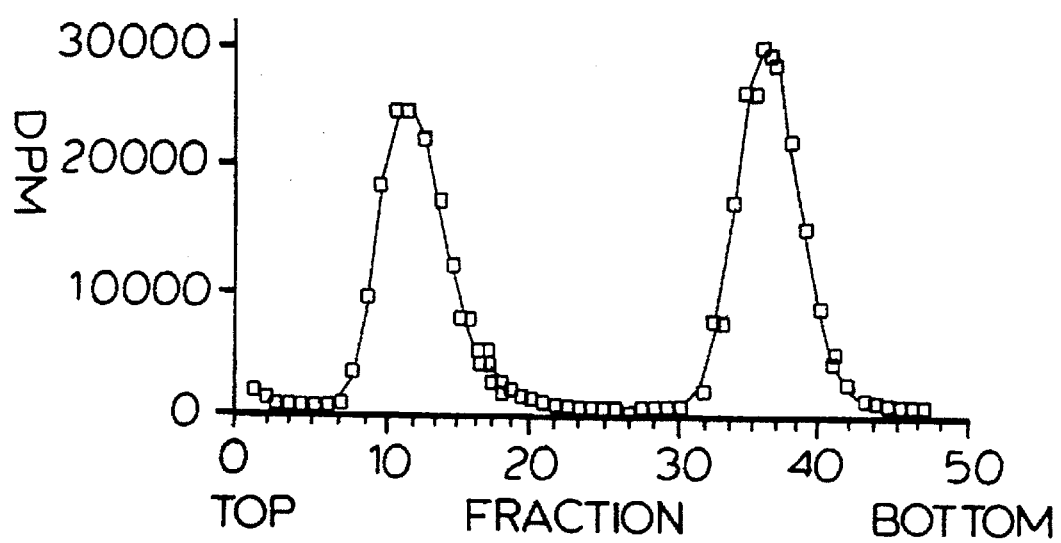
FIG. 9.

COLLECTION TIP FOR FRACTIONATING SOLUTION GRADIENTS

FIELD OF INVENTION

This invention relates to an apparatus for fractionating a solution gradient. In particular, this invention relates to a collection tip having a trumpet shape for fractionating a solution gradient.

BACKGROUND OF THE INVENTION

Solution gradients or density gradients are utilized in bio-chemical research to separate macromolecules such as proteins, DNA and RNA, and larger aggregates such as viruses and cells.

Solution gradients usually utilize a solute of varying concentrations to aid in the separation of particles. Examples of appropriate solutes are: sucrose, CsCl, Percoll™, ficoll, metrizamide, Nycodenz™, sodium acetate and/or glycerol. Particles are separated either by their velocity of sedimentation in a centrifugal field, or by their density in a centrifugal field if there is an isopycnic point within the solution column in the tube. Faster, or denser particles will appear lower in the tube.

After the sample has been subjected to the centrifuge, the particles are recovered from the gradient for analysis. Fractionation methods and apparatus used to recover the sample in the gradient involve the transfer of the entire gradient or certain layers or bands of the solution gradient to other vessels. It is often desired to extract only desired bands from the solution gradient for electron microscopy, liquid scintillation or gel electrophoresis.

One of the earliest and simplest methods of fractionation is to pierce the bottom of the centrifuge tube with a fine beveled needle and collect the drops of the solution gradient as it flows through the needle into a second vessel. The flow of the solution into the opening of the needle becomes conical. In other words, the particles directly in front of the needle opening and within the cone are drawn into the needle opening before particles outside the cone. The resulting fractionation of layers of the solution gradient does not have a high resolution.

Side hole needles have also been used for fractionation. Side hole needles have a hole on each side of the needle tip. Side hole needles are more effective than the beveled needle, but side hole needles also draw the solution into the needle in a conical fashion preventing high resolution of the fractionation.

Another method for fractionating solution gradients introduces a dense solution at the bottom of a holding tube which floats the gradient up to an inverted collection funnel. The vertical movement of the gradient causes contamination of some fractions with particles retarded near the wall of the holding tube, again preventing high resolution of the fractionation.

In U.S. Pat. No. 4,003,834 to Coombs, issued Jan. 18, 1977, an apparatus is disclosed for the fractionation of a solution gradient by displacement with a piston. The piston has a collection tip, which has a biconcave conical face, at its distal end. The tip has twelve collection holes about the surface of the tip. The piston is inserted into the centrifuge tube, urged downward against the solution, displacing the solution upwardly through the piston through the collection holes in the tip into a collection tube for transferring to another vessel. A rinse tube is disposed within the piston to allow for cleaning of the tip. Air pressure may be pumped into the piston through the rinse tube to transfer any solution gradient left in the piston to the second vessel.

While the apparatus disclosed in U.S. Pat. No. 4,003,834 has improved the resolution of the fractionation of a solution gradient, some mixing of the layers is still apparent during fractionation. Furthermore, the rinsing system of the U.S. Pat. No. 4,003,834 is susceptible to contamination during fractionation. Both factors contribute to limit the resolution of the fractionation.

SUMMARY OF THE INVENTION

The disadvantages of the prior art may be overcome by providing a collection tip for the fractionation of a solution gradient which has improved resolution of layers of the solution gradient as a result of minimizing any mixing of the layers during fractionation.

It is desirable to provide a collection tip for fractionation of a solution gradient which allows for isolation of individual layers of a solution gradient and maintains a high resolution of the layers of the solution gradients and minimal mixing of the layers after transfer thereof.

It is desirable to provide a collection tip having an internal passageway for transferring liquids, which passageway has a trumpet shape for enhancing laminar flow therethrough.

It is desirable to provide an improved rinsing system which minimizes contamination between fractions.

It is desirable to provide a check valve which facilitates rinsing of the collection tip.

In one aspect of the invention, there is provided a fractionation apparatus which has a displaceable piston operably mounted for displacing liquids from a tube as the piston is inserted therein. The fractionation apparatus has a tip which has a seal for sealingly engaging an inner wall of the tube and has an axially extending passageway for passing liquids from within the tube to a collector as the piston is inserted into the tube. The passageway is generally a trumpet shape having a wide end and a narrow end and a concave wall. The wide end is presented to the liquids and the narrow end connects to the collector. The trumpet shape enhances laminar flow of the liquid through the passageway.

In another aspect of the invention, there is provided a valve mounted in the narrow end of the collection tip for preventing flow of liquids back into the tube during rinsing.

In another aspect of the invention, there is provided a fractionation apparatus for the fractionation of a density gradient of liquids. The fractionation apparatus has a gradient holder having a centrifuge tube hole for receiving a centrifuge tube containing a density gradient of liquids having individual bands. A black, rigid displaceable piston is operably mounted relative to the gradient holder for inserting the piston into the centrifuge tube., A collection means is connected to the displaceable piston for collecting the density gradient. A rinsing means is connected to the displaceable piston for rinsing the collection means. An actuator means is connected to the displaceable piston for incrementally and accurately moving the displaceable piston into and out of the centrifuge tube. An illumination means illuminates the density gradient to determine the exact position of each individual particle band. The displaceable piston has a collection tip which has a seal to prevent liquids from escaping by the piston as the displaceable piston enters the centrifuge tube. The collection tip has an axially extending passageway for passing liquids from within the centrifuge tube to the collection means as the displaceable piston is inserted into the tube. The improvement comprises the passageway being generally a trumpet shape having a wide end and a narrow end with concave walls extending therebetween. The wide end is presented to the liquids and the narrow end connects to the collection means.

BRIEF DESCRIPTION OF THE DRAWINGS

The present invention will now be described in detail with reference to the accompanying drawings, in which:

FIG. 1 is a front elevational view of a fractionation apparatus incorporating the present invention having a piston for displacement of the solution gradient;

FIG. 2 is a cross-sectional front elevational view of the displaceable piston of FIG. 1;

FIG. 4 is a cross-sectional front elevational view of a ball valve for the collection tip of FIG. 3;

FIG. 5 is a top view of the gradient holder of the apparatus of FIG. 1;

FIG. 6 is a cross sectional view of the gradient holder of FIG. 5 taken along lines VI—VI;

FIG. 8 is a graph illustrating the gradient of a T4 phage virus with and without tail fibers using a fractionation tip of the prior art; and FIG. 9 is a graph illustrating the gradient of a T4 phage virus with and without tail fibers using the collection tip of FIG. 3;

DETAILED DESCRIPTION OF THE PREFERRED EMBODIMENT

Figure 3:
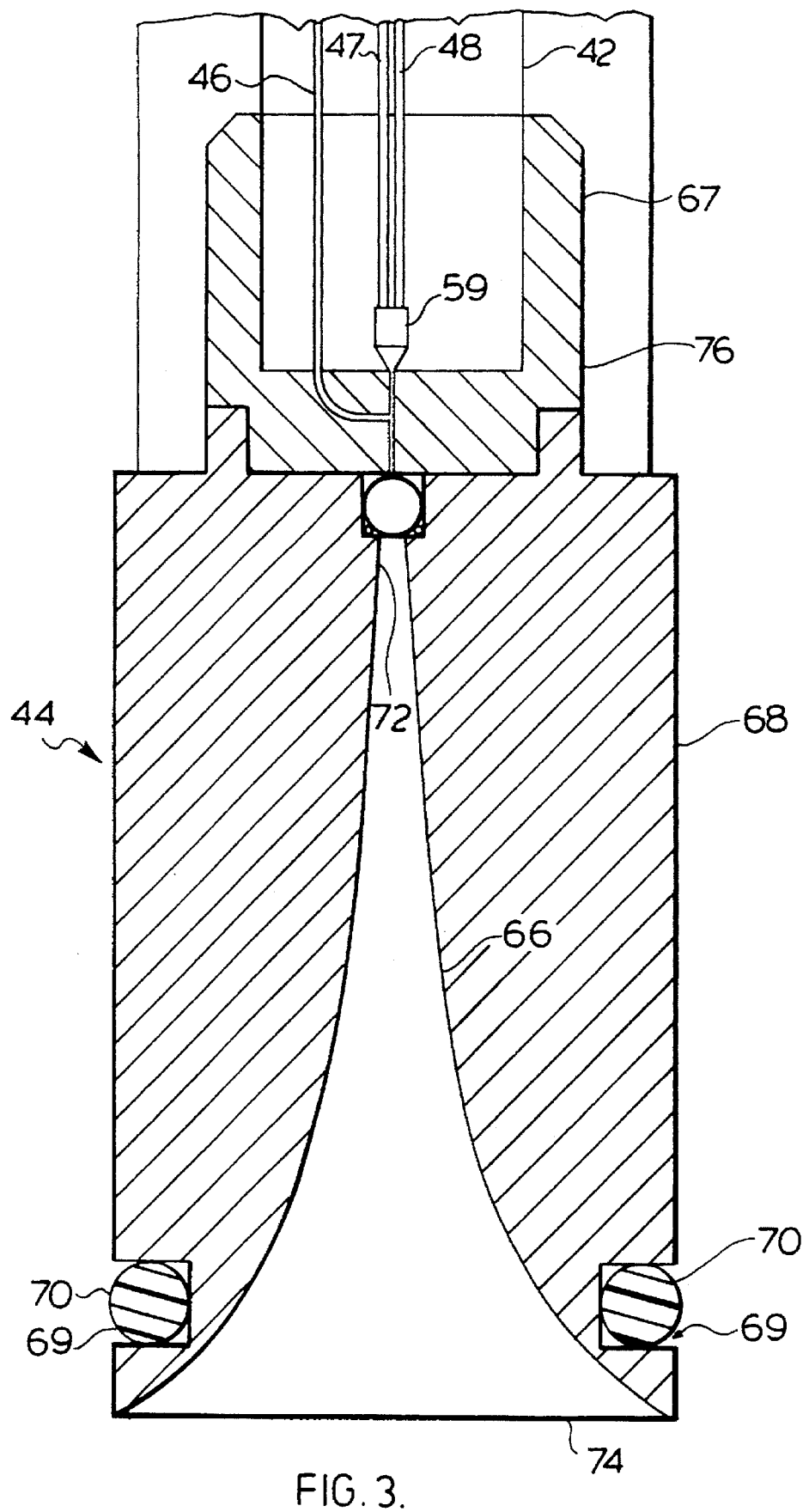
FIG. 3 is a cross-sectional view of the collection tip of the present invention.

A displaceable piston fractionation apparatus 10 is shown in FIG. 1. The fractionation apparatus 10 has a working stage 12 which serves as a housing for the apparatus and ensures a stable environment for undertaking a fractionation process. Working stage 12 comprises a top 14, a pair of support bars 16, a back support plate 18, and a base 20. The working stage 12 is made of any durable material, preferably aluminum.

An illumination source 22 is disposed below the working stage top 14 within the working stage 12. Any standard commercial light source may be used as long as its size is appropriate in relation to the size of the fractionation apparatus 10. However, if very hint minor bands are to be detected, a more powerful light source should be incorporated.

A light hole 24 is provided in top 14 to enable a beam of light to pass through and illuminate the density gradient. To protect the untempered lens of the illuminator source 22 from accidental spills, an optically clear cover can be placed over the lens.

A solution gradient holder 26 is affixed on the top 14 above light hole 24 and in alignment with the illumination source 22. Holder 26 has a base 28 and top 30. The construction of holder 26 is described below in greater detail.

Extending upwardly from the working stage top 14 is a framed support stand 32. A worm gear actuator 34 is mounted at the upper end of the support stand 32. Worm gear actuator 34 has a shaft 36 having a handle 38 for rotating the shaft. Engaging the shaft 36 is a vertically extending shaft 40. Shaft 40 is in axial alignment with the gradient holder 26 and the light hole 24. Rotation of the shaft 36 causes the shaft 40 to move towards and away from the working stage top 14.

Figure 10:
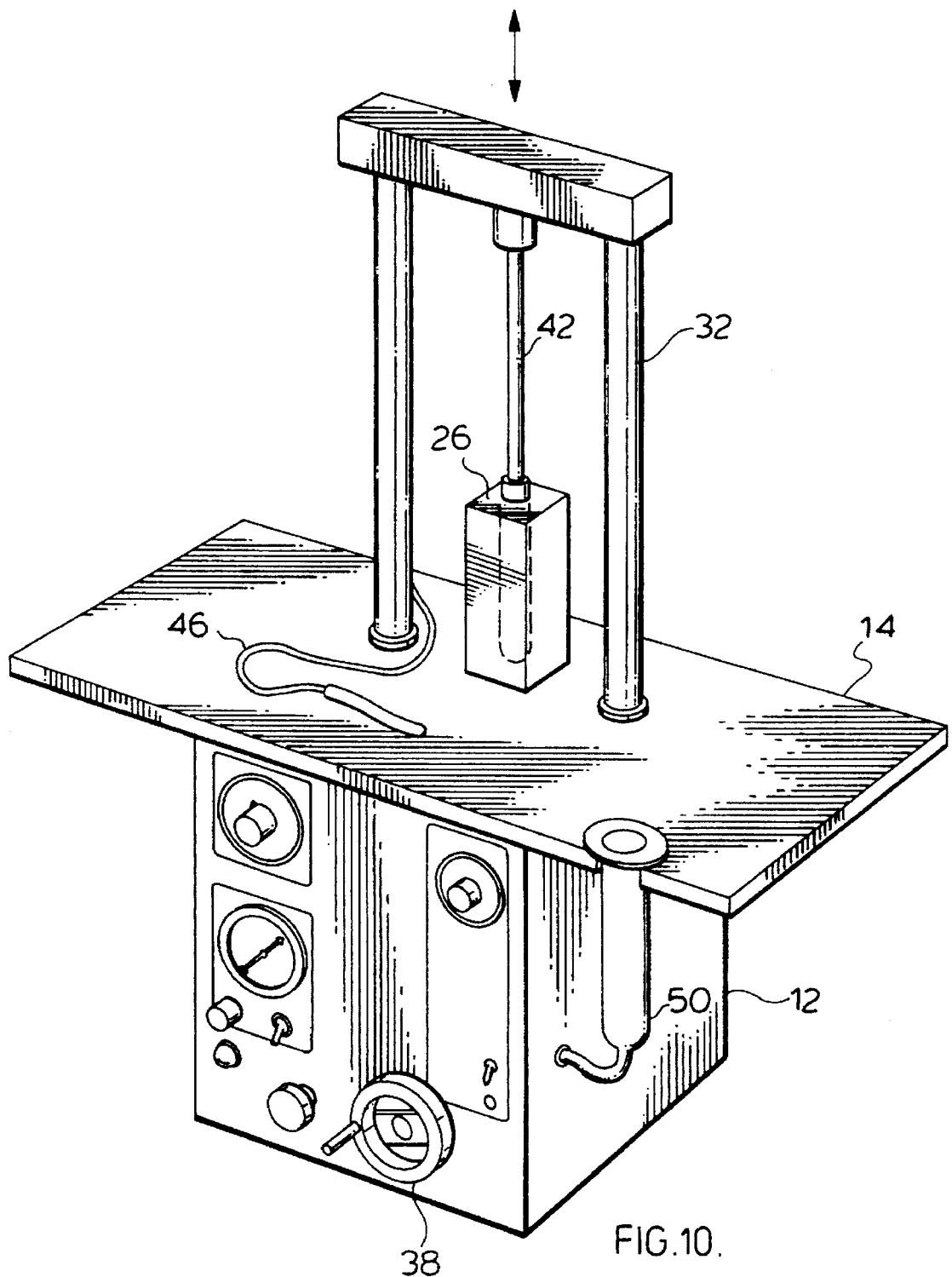
FIG. 10 is a perspective view of a second embodiment of a fractionation apparatus incorporating the collection tip of FIG. 3.

Although the apparatus 10 has been illustrated with the worm gear actuator 34 mounted above the top 14, it is understood that the mechanism could be installed below the top and within the housing 12, as illustrated in FIG. 10. Further, the apparatus could be fully automated by incorporating a computer for controlling the operation of the apparatus. An encoder can be mounted on shaft 36 to produce a digital signal proportional to the rotation of the shaft 36 to provide an accurate rotational reference signal. The computer can be operably connected to a motor in a drive train to provide precise positioning and velocity of piston movement.

Piston 42 is mounted on the end of vertical shaft 40. Piston 42 has an interchangeable collection tip 44 mounted at the end thereof. Piston 42 has a collection tube 46, an air tube 47, and a rinse tube 48 connected thereto. Rinse tube 48 is connected to a rinse reservoir 50. The rinse reservoir 50 contains a suitable type of buffer solution for rinsing and cleansing the collection tube 46 before and after the withdrawal of each individual band. Air tube 47 is connected to pump 52, which forces air into the piston 42. The pump 52 may be an air pump or other means which provides air pressure. Pump 52 blows air through the air tube 47 to remove the rinse from the collection tube 46.

It is also understood that the operation of the pump 52 could be operated in a variety of modes, including adding a potentiometer to the enabling circuit to control the pressure generated by the pump. A pump could also be added to the rinse reservoir 50 so that the buffer solution could be pumped into the rinse tube 48 rather than by manual operation.

Referring to FIG. 2, the end of the shaft 40 has a screw thread for detachably receiving piston 42. The upper end of piston 42 has a threaded bore for threadingly engaging shaft 40. The lower end of piston 42 has a threaded counterbore. The piston 42 has one internal passageway 54 communicating between the upper end and the counterbore of the lower end of the piston 42. Inserted within the passageway 54 are the collection tube 46, the air tube 47 and rinse tube 48, respectively. The air tube 47 and the rinse tube 48 are connected to a check valve 59 at the top of the collection tip 44. The check valve 59 prevents back flow of buffer solution and air.

Referring to FIG. 3, the collection tip 44 of the present invention is illustrated. The collection tip 44 has a body portion 68 and a connection portion 67. Body portion 68 has a central axial passageway 66. The diameter of the body portion 68 of the tip 44 is varied to accommodate different sizes of centrifuge tubes. The length of the tip is varied proportionately. The body portion 68 has a malleable O-ring 70 in circumferentially extending groove 69. When tip 44 is being inserted into a centrifuge tube, a seal is established between the collection tip and tube, so that no liquid can escape around the tip as it is lowered into the tube.

Preferably, the collection tip 44 and piston 42 should be constructed of black material to minimize glare.

The axial passageway 66 is of a unique trumpet shape. Along the length of the passageway, moving away from narrow end 72, the radius of the passageway 66 slowly increases as a function of length and then exponentially increases presenting a wide end 74 presenting convex walls.

The trumpet shape enhances a laminar flow of liquids through the entire length of the collection tip 44.

At the narrow end of passageway 66 is a counterbore 71 which has a slightly larger diameter than the narrowest diameter of the narrow end. Seated within this bore is a ball 81. Flow of liquid from the wide end to the narrow end of the passageway 66 will be allowed to pass by ball 81. Reverse or backflow will urge the ball 81 to become seated within the base of the counterbore 71 closing the narrow end of the passageway 66. An O-ring 75 is seated beneath the ball to create a malleable seal for the ball to ensure a sealing engagement.

FIG. 4 illustrates a second embodiment of the ball valve 80 mounted in the narrow end of passageway 66 in detail. The ball valve 80 includes a ball 81 resting on an O-ring 78. Above the ball 81 is a cap 76 which has a central opening 79. Cap 76 is threaded into a threaded bore at the end of passageway 66. The depth of the threaded bore is sufficient to allow ball 81 to axially move after the cap is fully registered within the threaded bore. When the liquid is drawn up into the collection tube 46, the ball is displaced vertically, the liquid passes around the ball and through the central opening 88.

Referring to FIGS. 5 and 6, the gradient holder 26 is designed to optimize band visibility while holding a tube firmly during fractionation. The laminated holder top is made of two substantially rectangular sections 82 and 84. Section 84 is situated in the foreground of the gradient holder 26 and should be constructed of a transparent material such as PLEXIGLAS. The second section 82 of the gradient holder 26 should be constructed of a black material and is used to produce a dark background for the density gradient. A centrifuge tube hole 86 is drilled near the interface of these two sections so that approximately ¾ of the circumference of the hole lies in the black second section 82 and about ¼ of the circumference lies in the transparent plastic section 84. Alternatively, the black second section 82 can be bored out to fit the centrifuge tube and a flat window can be screwed on the front of the groove as shown in FIG. 5. Screws 89 are provided to reinforce the bonded transparent plastic section 84 and the black section 82. The polished transparent surface thus provides a window for the gradient, otherwise surrounded in black.

A transparent plug 90 having a flat window, is inserted into the base 28 of the gradient holder 26 for tube support and illumination. The window provides illumination over the length of the gradient, thus ensuring a proper illumination of all of the individual bands appearing in the gradient.

The above described displaceable fractionation apparatus incorporating the present invention operates in the following manner. The rinse tube 48 and the collection tube 46 are connected to the collection tip 44 and are threaded through the piston 42. The rinse reservoir 50, is filled with standard rinse buffer solution, and the rinse pump is primed.

A large syringe is filled with water or 5% glycerol and then inserted into the tube hole 86. Liquid is injected into the tube hole. A centrifuge tube 100 is then placed into the holder 26 until the water or 5% glycerol rises just to the top of the centrifuge tube 100. The film of liquid between the tube and the centrifuge hole 86 reduces the glare. The centrifuge tube 100 must be pre-tested for holder fit and must have the sharp inner edge of the rim scraped off to prevent damage to the O-ring 70. Light lubrication of the O-ring 70 is also advised.

Furthermore, the centrifuge tube 100 may be locked into position in the holder 26. A cap, with two pins on opposite sides of the cap, is placed on centrifuge tube 100, and when centrifuge tube 100 is inserted into the holder 26, the pins are engaged with grooves in the wall of the holder 26 and the centrifuge tube 100 will be locked into position when the tube 100 and cap are rotated into engagement with the grooves.

Whole gradient fractionation in constant volume aliquots can be accomplished utilizing this invention by lowering the piston 42 into the density gradient and discontinuously operating the handle 38. The volume displaced employing this method is determined by the diameter of the gradient and the fraction, or number of turns per sample. Alternatively, a computerized stepper motor may be added to the drive train to give precise control of fraction distance and piston speed (FIG. 10).

If, however, isolation of individual bands is desired, the illuminating means 22 is switched on and the exact position of each individual band is marked on a tape 92 applied next to the gradient, and then the piston 42 is carefully lowered until the upper edge of the band is just hidden. A buffer solution is pumped through the rinse line 48 to the collection line 46, followed by air to remove the rinse. The piston 42 is slowly lowered through the band.

The fraction is collected until the piston 42 has displaced the entire band. After each band has been displaced air is introduced to remove sample from the collection line 46 and the piston is then lowered to the top of the next band and the tubing is again rinsed and blown dry. When the fractionation is completed, the piston 42 is raised and the centrifuge tube 100 is removed from the gradient holder. A rinse of distilled water and acetone following use of the fractionation apparatus will prevent growth of algae in the tubing.

Figure 7:
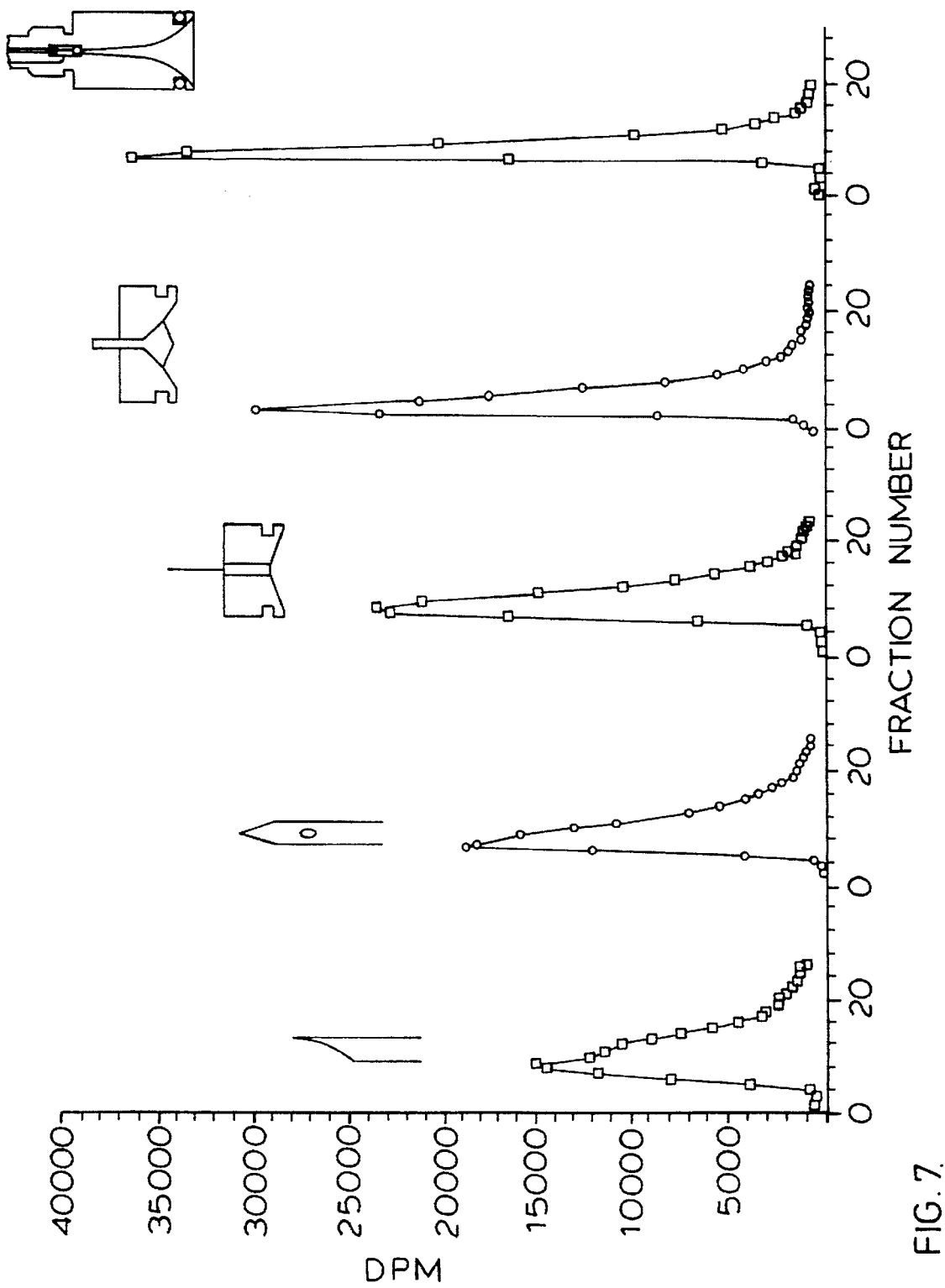
FIG. 7 is a graph comparing fractionation of a virus band using four prior art tips against the collection tip of FIG. 3.

FIG. 7 is a graph comparing the results of five identical gradients of a T4 phage virus which was fractionated by four prior art collection tips and the collection tip of the present invention. All collection tips were employed using the motorized fractionator apparatus as illustrated in FIG. 10, operating at identical speeds of displacement.

To facilitate this test, the beveled needle and side-holed needle were inserted into the shallow cone needle so that the needle tip of the beveled needle and side-holed needle overhung the shallow cone needle by approximately 5 min. Peak A illustrates the result using a beveled needle. Peak B illustrates the result using a side-holed needle. Peak C illustrates the result using a shallow cone. Peak D illustrates the result using a biconcave cone as described in U.S. Pat. No. 4,003,834. The fractionation of the virus using the collection tip of the present invention is shown as peak E.

According to FIG. 7, the number of fractions required to remove the entire virus band using the five different collection tips is approximately 14, 14, 12, 10 and 9 from A-E, respectively. The decreased fraction number when using the collection tip of the present invention indicates that there has been a substantial improvement in resolution of the layers of the solution gradient being fractionated and, therefore, decreased mixing of the layers of the solution gradient has occurred during fractionation.

Referring to FIGS. 8 and 9, the resolving power of the collection tip of the present invention is illustrated. FIGS. 8 and 9 illustrates the dramatic improvement for harvesting gradients, particularly where more than one virus or macromolecule are present within the solution gradient. Prior art collection tips, as illustrated in FIG. 8, have heretofore been unable to achieve the required resolution in order to distinguish between nearby peaks of macromolecules. The first peak of each diagram is a tailed T4 phage virus and the second peak is a tailless T4 phage virus. The peaks in FIG. 9 are smooth and monodisperse, indicating that each arises from a single particle type. The lack of scatter in the data indicates that the same amount of sample is being removed for each fraction.

Although the disclosure describes and illustrates the preferred embodiments of the invention, it is understood that the invention is not limited to these particular embodiments. Many variations and modifications will now occur to those skilled in the art. For definition of the invention, reference is made to the appended claims.

I claim:

1. A fractionation apparatus for fractionation of a density gradient contained in a robe, said fractionation apparatus having a displaceable piston operably mounted for displacing liquids from the tube as the piston is inserted therein, and comprising a collection tip having a seal desposed for sealingly engaging an inner wall of said tube and having an axially extending passageway for passing liquids from within the tube to a collector as said piston is inserted into said tube, the improvement comprising said passageway being generally elongate and having a wide end and a narrow end, said passageway narrowing smoothly and convexly from said wide end to said narrow end for enhancing laminar flow therethrough, said wide end for presenting to said liquids and said narrow end far connecting to said collector.

2. A fractionation apparatus as claimed in claim 1 wherein said collection tip further comprises a valve mounted in the narrow end for preventing flow of liquids back into the tube.

3. A fractionation apparatus as claimed in claim 2 wherein said valve is a ball type valve.

4. A fractionation apparatus for the fractionation of a density gradient of liquids comprising:

a gradient holder having a centrifuge tube hole configured for receiving a centrifuge tube containing a density gradient of liquids having individual bands;

a black, rigid displaceable piston operably mounted relative to the gradient holder for inserting the piston into the centrifuge tube;

a collection means connected to the displaceable piston for collecting the density gradient;

a rinsing means connected to the displaceable piston for rinsing the collection means;

an air pressure means for injecting air into the collection means using contents thereof out of the collection means;

an actuator means connected to the displaceable piston for incrementally and accurately moving the displaceable piston into and out of the centrifuge tube; and an illuminating means for illuminating the density gradient to determine the exact position of each individual band; said displaceable piston having a collection tip which has a seal to prevent liquids from escaping by the piston as said displaceable piston is displaced within the centrifuge tube and which has an axially extending passageway for pushing liquids from within the centrifuge tube to the collection means as said displaceable piston is inserted into said tube, the improvement comprising said passageway being generally elongate and having a wide end and a narrow end, said passageway narrowing smoothly and convexly from said wide end to said narrow end for enhancing laminar flow therethrough, said wide end for presenting to said liquids and said narrow end for connecting to said collector.

5. A fractionation apparatus as claimed in claim 4, wherein said rinsing means comprises a rinse tube and an air tube, wherein the rinse tube is connected at one end to a rinse reservoir containing a rinse solution and is connected at the other end to the displaceable piston for rinsing the collection means, and wherein one end of the air tube is connected to a supply of pressurized air and the other end is connect to the displaceable piston for removing the rinse solution and sample from the collection means.

6. A fractionation apparatus as claimed in claim 5 wherein said valve is a ball type valve.

7. A fractionation apparatus as claimed in claim 4 wherein said collection tip further comprises a valve mounted in the narrow end for preventing flow of liquids back into the centrifuge tube.

* * * * *